United States Patent [19]
Russell

[11] Patent Number: 5,337,419
[45] Date of Patent: Aug. 16, 1994

[54] FACE PROTECTOR

[75] Inventor: John P. Russell, Gardendale, Ala.

[73] Assignee: Infection Control Products, Inc., Gardendale, Ala.

[21] Appl. No.: 950,821

[22] Filed: Sep. 24, 1992

Related U.S. Application Data

[63] Continuation-in-part of Ser. No. 933,522, Aug. 24, 1992, and a continuation-in-part of Ser. No. 933,510, Aug. 24, 1992.

[51] Int. Cl.$^5$ .............................................. A42B 3/22
[52] U.S. Cl. .................................................... 2/9; 2/8; 2/206; 2/424; 128/857
[58] Field of Search ..................... 2/7, 8, 9, 10, 11, 12, 2/15, 173, 206, 410, 424; 128/846, 857, 858; 403/117

[56] References Cited

U.S. PATENT DOCUMENTS 2,487,848  11/1949  Bowers ........................................ 2/8
4,047,249   9/1977  Booth ........................................ 2/424
4,853,974   8/1989  Olim ......................................... 2/206

FOREIGN PATENT DOCUMENTS 2215584  9/1989  United Kingdom ..................... 2/12

Primary Examiner—Clifford D. Crowder
Assistant Examiner—Diana L. Biefeld
Attorney, Agent, or Firm—George A. Bode

[57] ABSTRACT

A face protector for shielding the face of the wearer while permitting observation and pivoting of the shield toward and away from the face comprising: an elongated flexible band of absorbent padding sized and adapted to, be fitted about the forehead; a first elongated flexible stiffening member attached therealong to a corresponding confronting portion of the band; a second elongated stiffening member having a length greater than the first stiffening member and pivotally attached to the first stiffening member at corresponding end portions of the stiffening members so that the stiffening members are spaced apart when the band is fitted about the head; a flexible transparent face shield with an integral anti-glare, anti-fog coating connected at a top portion thereof to the second stiffening member along its length whereby pivotal movement of the second stiffening member relative to the first stiffening member permits movement of the shield toward and away from the face; and, a void provided in one end portion of the second stiffening member for accepting the corresponding end portion of the first stiffening member, thereby limiting the pivoting movement of the second stiffening member relative to the first stiffening member and the shield toward the face.

19 Claims, 6 Drawing Sheets

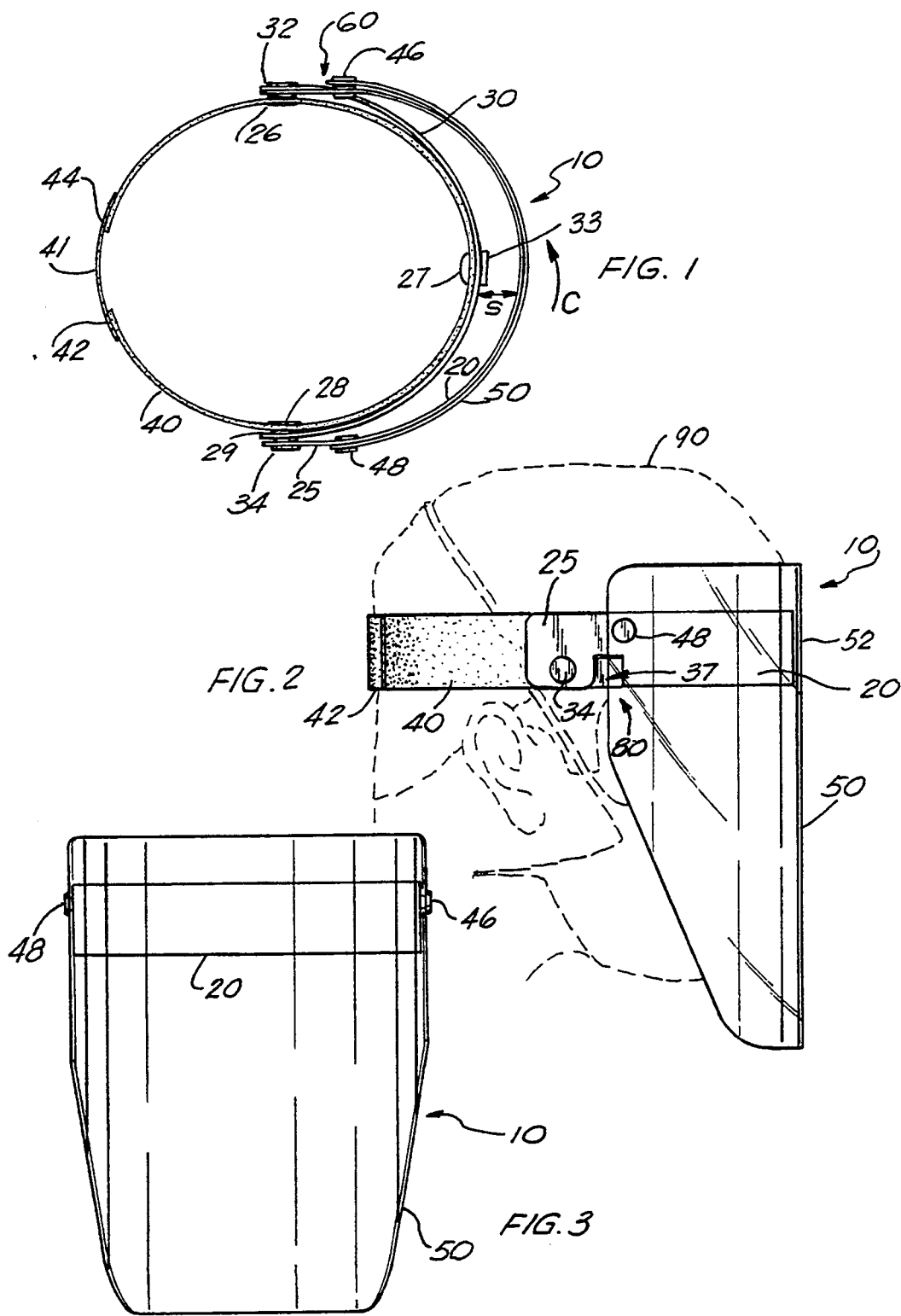

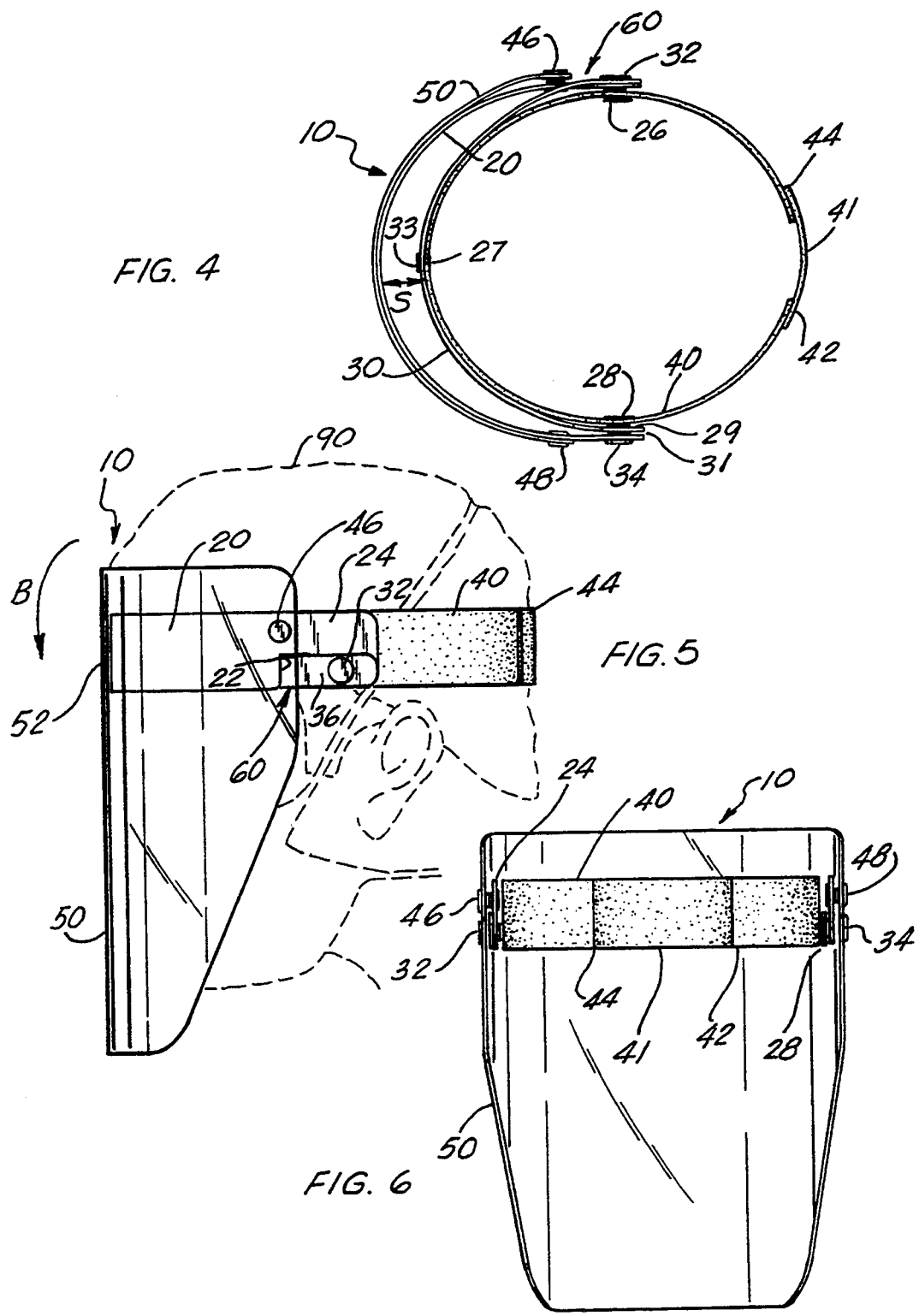

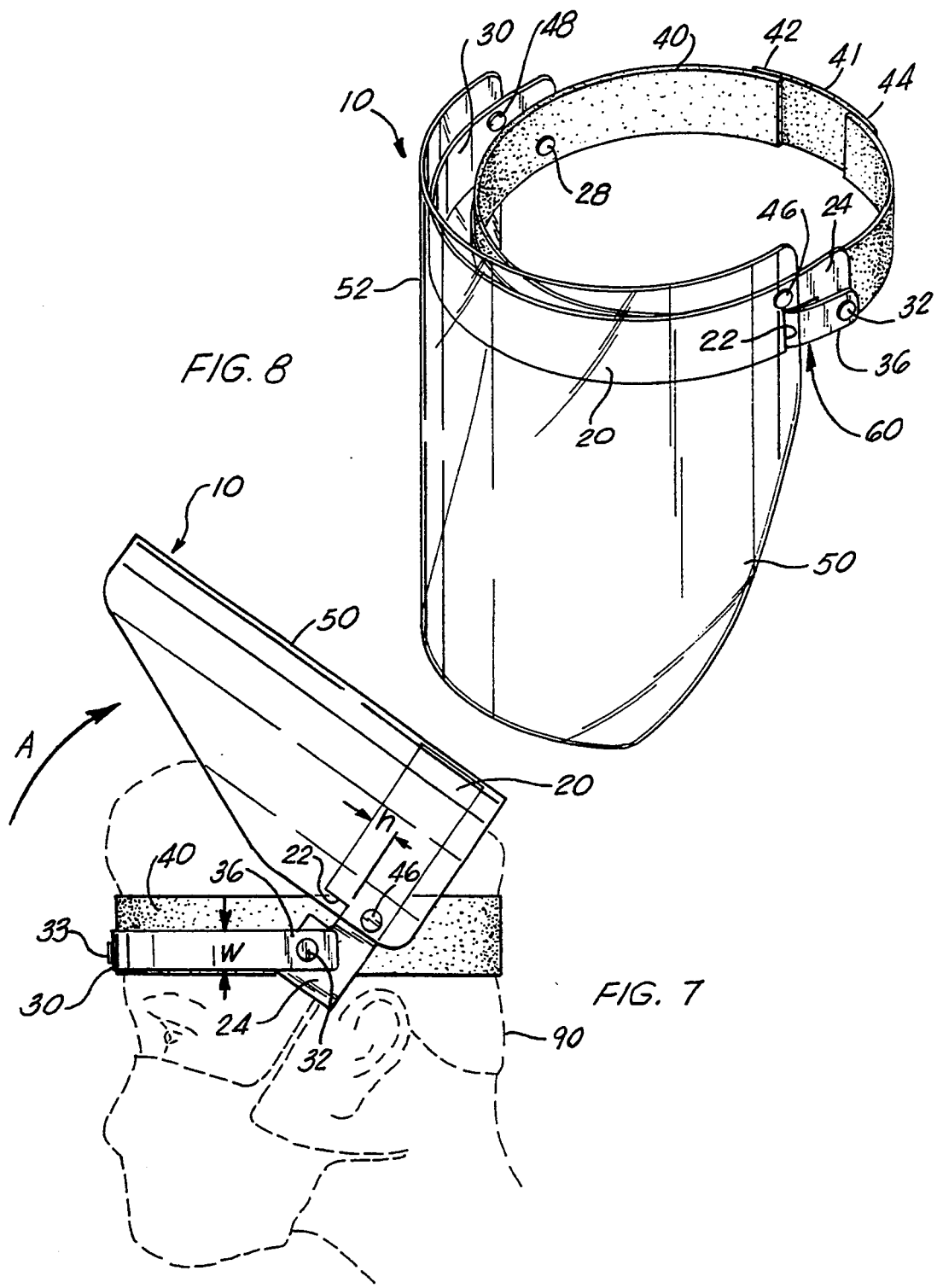

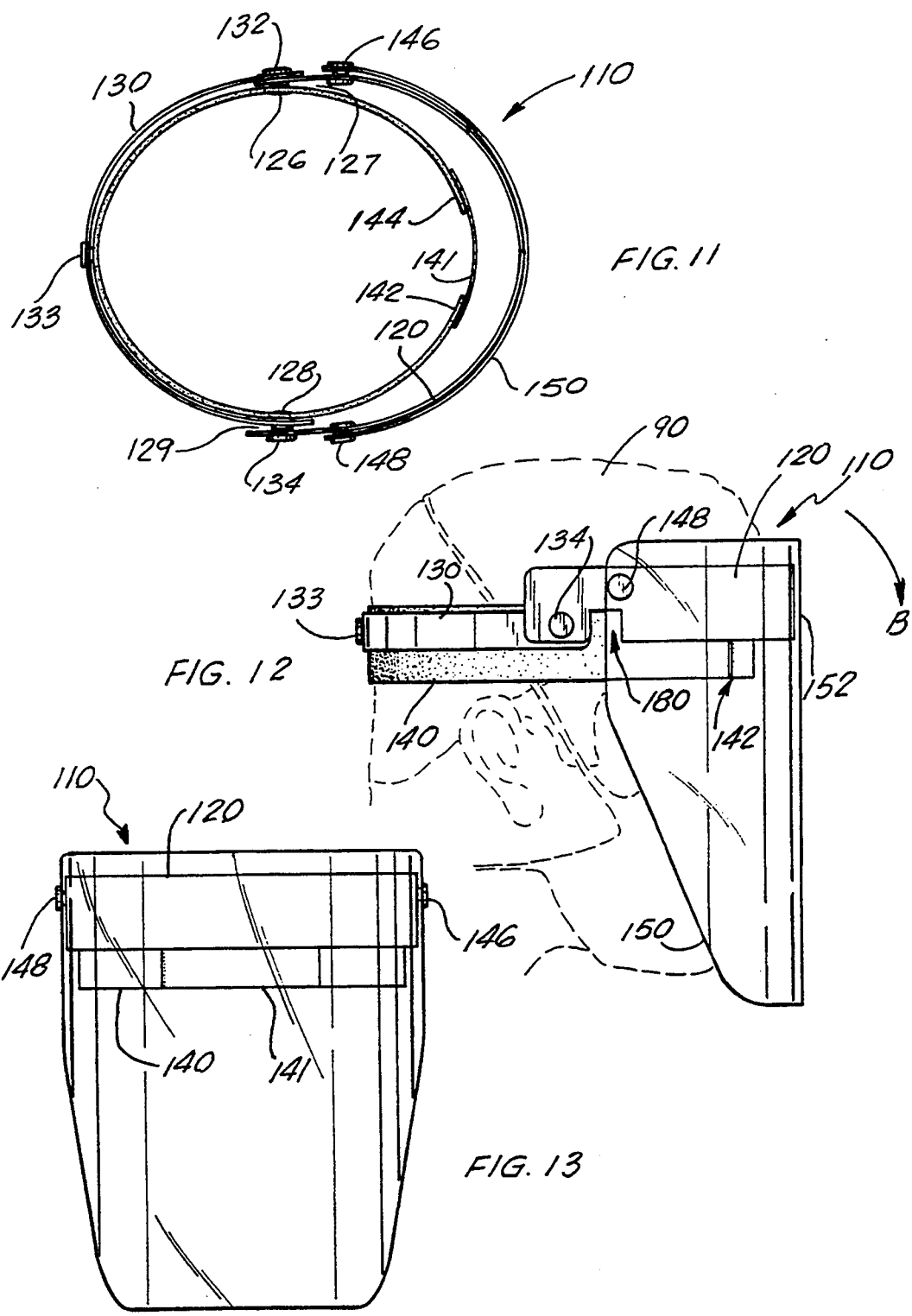

FACE PROTECTOR

This application is a continuation-in-part application of previous applications by the same inventor bearing U.S. Ser. No. 07/933,522, filed Aug. 24, 1992, and 07/933,510, filed Aug. 24, 1992. The entire previous applications Ser. No. 07/933,522 and 07/933,510 are incorporated herein by reference as if set forth in full below.

BACKGROUND OF THE INVENTION

1. Field of the Invention

The present invention relates generally to face protectors and, more particularly to a face protector for shielding the face of the wearer while permitting observation and pivoting of the shield toward and away from the face, and even more particularly, pivoting on the shield toward and away from the face, but limiting the pivoting movement of the shield toward the face.

2. General Background in the operating room and other medical situations such as emergency room and field treatment: the full face and its cavities must be protected from the splashing of blood and other bodily fluids to protect the medical care providers should the patient have HIV, AIDS or other infectious diseases. It is well known to provide a transparent face shield connected to some form of headband. However, once the flow of blood or other fluid has been stopped there may be a need lift or flip up the face shield so that the medical care provider has unobstructed visual or oral access to the patient or sanitary access to his own face.

A need, therefore, exists for a face protector which permits shielding of the face of the wearer while permitting observation and yet allows pivoting of the shield toward and away from the face.

It is a principal object of the present invention to meet the foregoing need by providing such a face protector.

It is yet another object of the present invention to provide a means for limiting the pivoting movement of the shield toward the face so that a proper spacing is always provided between the face and the shield.

It is yet still another object of the present invention to provide a face protector with an integral anti-glare, anti-fog transparent face shield.

It is a further object of the present invention to provide a headband with an absorbent pad to accumulate perspiration from the wearer's forehead.

It is still a further object of the present invention to provide a face protector commensurate with the aforementioned objects that is simple and economical in design yet extremely durable and safe to use.

The above and other objects and advantages of this invention will become more readily apparent when the following description is read in conjunction with the accompanying drawings.

SUMMARY OF THE PRESENT INVENTION

The preferred embodiment of the apparatus of the present invention solves the aforementioned problems in a straightforward and simple manner. What is provided is a face protector for shielding the face of the wearer while permitting observation and pivoting of the shield toward and away from the face comprising: an elongated flexible band of absorbent padding sized and adapted to be fitted about the head; a first elongated flexible stiffening member attached therealong to a corresponding confronting portion of the band; a second elongated stiffening member having a length greater than the first stiffening member and pivotally attached to the first stiffening member at corresponding end portions of the stiffening members so that the stiffening members are spaced apart when the band is fitted about the head; a flexible transparent face shield with an integral anti-glare, anti-fog coating connected at a top portion thereof to the second stiffening member along its length whereby pivotal movement of the second stiffening member relative to the first stiffening member permits movement of the shield toward and away from the face; and, means for limiting the pivoting movement of the second stiffening member relative to the first stiffening member and the shield toward the face.

BRIEF DESCRIPTION OF THE DRAWING

For a further understanding of the nature and objects of the present invention, reference should be had to the following description taken in conjunction with the accompanying drawing in which like parts are given like reference numerals and, wherein:

FIG. 1 is a top plan view of the preferred embodiment of the apparatus of the present invention, with the face shield in the "down" position;

FIG. 2 is a right side elevational view of the embodiment of FIG. 1, adapted to the head of a user (IN PHANTOM);

FIG. 3 is a front elevational view of the embodiment of FIG. 1;

FIG. 4 is a bottom plan view of the embodiment of FIG. 1;

FIG. 5 is a left side elevational view of the embodiment of FIG. 1, adapted to the head of a user (IN PHANTOM);

FIG. 6 is a rear elevational view of the embodiment of FIG. 1;

FIG. 7 is a left side elevational view of the embodiment of FIG. 1, with the face shield pivoted to an "up" position and adapted to the head of a user (IN PHANTOM);

FIG. 8 is a top frontal perspective view of the embodiment of FIG. 1;

FIG. 11 is a top plan view of the embodiment of FIG. 9;

FIG. 12 is a right side elevational view of the embodiment of FIG. 9 adapted to the head of a user (IN PHANTOM);

FIG. 13 is a front elevational view of the embodiment of FIG. 9;

DETAILED DESCRIPTION OF THE PREFERRED EMBODIMENT

Figures 9, 10:
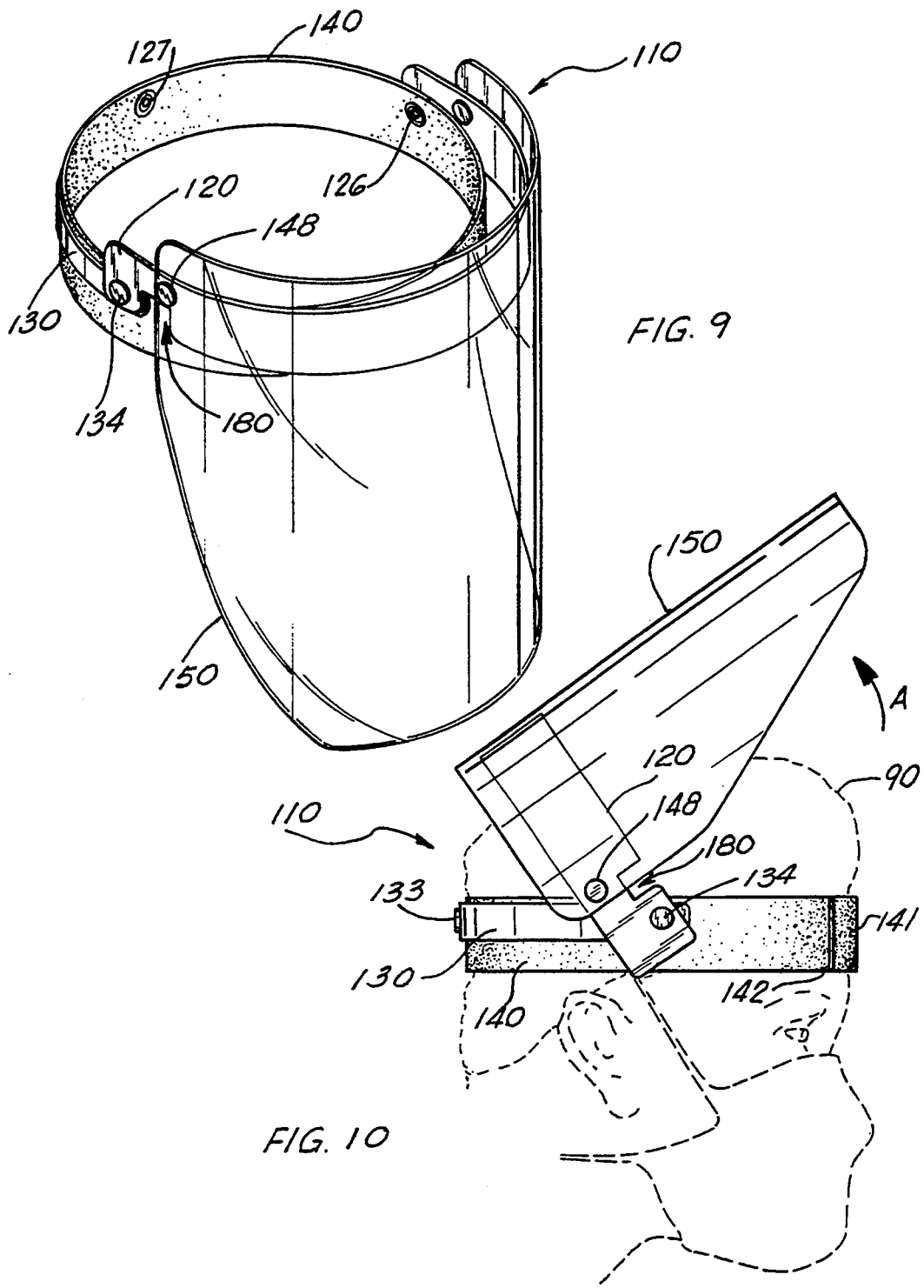
FIG. 9 is a top frontal perspective view of an alternate embodiment of the apparatus of the present invention.
FIG. 10 is a right side elevational view of the alternate embodiment of FIG. 9, with the face shield pivoted to an "up" position and adapted to the head of a user (IN PHANTOM)
Figure 14:
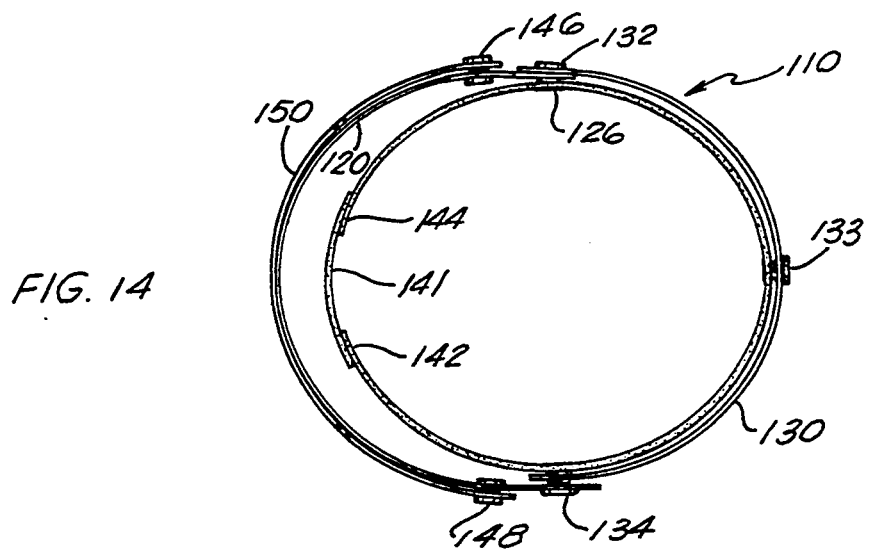
FIG. 14 is a bottom plan view of the embodiment of FIG. 9.
Figure 15:
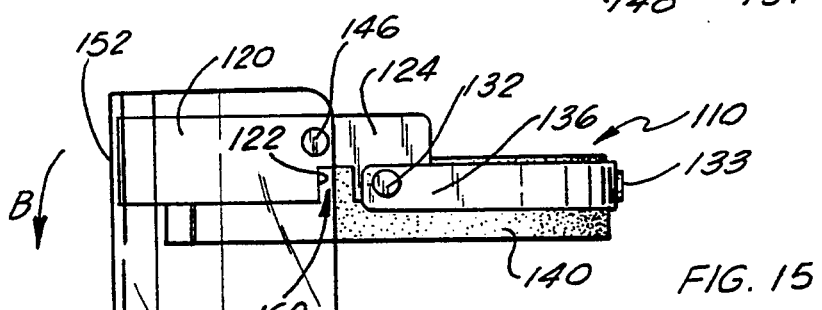
FIG. 15 is a left side elevational view of the embodiment of FIG. 9.
Figure 16:
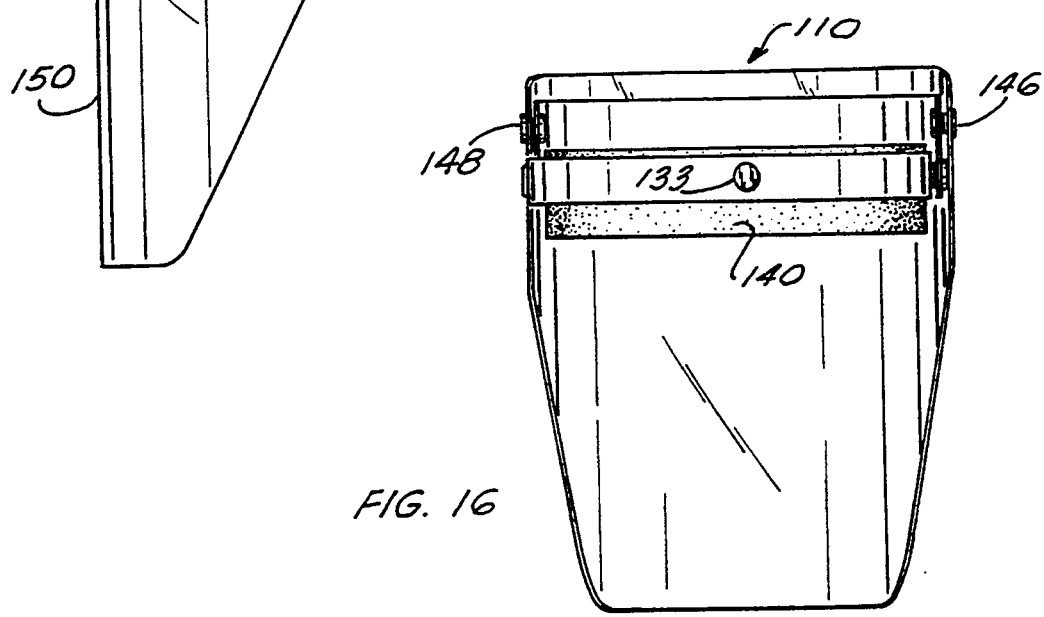
FIG. 16 is a rear elevational view of the embodiment of FIG. 9.

Referring now to the drawings, and in particular FIGS. 1 and 8, the preferred embodiment of the apparatus of the present invention is designated generally by the numeral 10. For purposes of illustrating the preferred embodiment of the present invention, face protector 10 is shown in FIGS. 2, 5 and 7 as fitted on the head of a human wearer 90 (in PHANTOM). The term "forehead" as used herein should be interpreted broadly to include the upper portion of the head above the eyebrows.

Face protector 10 comprises, as best seen in FIGS. 1, 2, 5, 7 and 8, an elongated generally rectangular flexible band 40 adapted to be fitted and fastened about the head, particularly the forehead. Flexible band 40 is made of an absorbent padding such as "CONFORM" (manufactured by Kimberly-Clark), capable of absorbing perspiration of the wearer 90. Headband 40 can be opened and fastened for application, removal or adjustment from the head of the user 90 by conventional VELCRO fastening means 42, 44 (typical corresponding male and female or hook and loop members). Further, a length of stretchable or elastic material, 41 can be inserted between VELCRO fastening means 42, 44 so that band 40 is effectively stretchable or expandable as worn.

As best seen in FIGS. 1, 2, 4, 5, 7 and 8, a first elongated generally rectangular flexible band or stiffening member 30 is attached at selected points along its length member 30 to a corresponding confronting portion of band 20. Band 30 is made of a commercial plastic or high impact styrene plastic so that it is stiffer than band 20. It is an elongated generally rectangular member which is preferably fastened at both ends and at its mid-point to band 20. The end fastenings 26, 32 and 28, 29 are best seen in FIGS. 1 and 4 and take the form of conventional mating buttons-type or snap fasteners. In this way, absorbent band 20 can be replaced when it is saturated with perspiration of the user. Fastening means 27, 33, as best seen in FIGS. 1 and 4, provide fastening between band 20 and first stiffening member 30 at the corresponding mid-point of the arc formed by band 30. Also, as seen in FIGS. 1, 2, 4, 5, 7 and 8, the length of first flexible stiffening member 30 corresponds to substantially half the length of band 20, the length 30 thus corresponding to the frontal half portion of band 20 after it has been fitted about the forehead of user 90.

As best seen in FIGS. 1, 2, 4, 5, 7 and 8, a second elongated generally rectangular flexible band or stiffening member 20 having a length greater than first stiffening member 30 is pivotally attached to the first stiffening member at corresponding end portions 24, 25 and 36, 37. By this pivotal connection band 20 is also pivotally connected to headband 40 by fastening means 26, 32 and 28, 29, 31, 34. This arrangement causes band 20 to "bow out" relative to connected bands 30 and 40 thus providing, as best seen in FIGS. 1, 4 and 8, a different curvature for bands 20 and 30 and tensioning and spacing between them when band 40 is fitted about the head of user 90 and all-button type or snap fasteners (26, 28 and 32, 29 and 31, 34) are connected.

The special arrangement of bands 20 and 30 can best be seen in FIGS. 1, 2, 4, 5, 7 and 8. At end portions 25 and 37, band 20 is positioned exteriorly of band 30. This relationship continues along bands 20 and 30 (in the direction of ARROW C in FIG. 1) until near end portions 24, 36 of bands 20, 30, respectively, where bands 20,30 cross so that band 20 is positioned interiorly of band 30. Thus, at end portions 25, 37 band 30 fastens to band 40 and band 20 fastens to band 30 and at end portions 24, 36 band 20 fastens to band 40 and band 30 fastens to band 20. This crossing arrangement at end portions 24, 36 will be described further herein.

As best seen in FIGS. 2, 3 and 5–8, a transparent face shield 50 is connected along its top portion 52 to the external surface of second stiffening member 20. Connection is by conventional button-type snap fasteners 46, 48, although other fasteners may be used even gluing or heat sealing. Face shield 50 is adapted in size and shape to cover the entire face from the forehead area to below the chin (although other embodiments are envisioned where the shield can cover only the eyes, or, only the eyes and nose, to allow the mouth area to be open (for instance, verbal communication may be necessary between the medical care provider and assistants or oral communication may be necessary between the medical care provider and the patient)). The face shield 50 is made of an impact resistant and transparent plastic or polyester, of optic grade or polymer film, with a chemical coating or film provided on both sides for preventing fogging and glare by light reflection. The coating agents can be a silicone agent such as a dimethylsiloxane polymer.

As best seen in FIGS. 2, 5, 7 and 8, pivotal movement of second stiffening member 20 relative to first stiffening member 30 permits movement of shield 50 toward and away from the face of the wearer 90. As seen in FIGS. 5 and 7, movement of the shield in the direction of ARROW "A" pivots the shield about fasteners 26, 32 and 28, 29 and 31, 34 so that the face of the user is exposed. From the "up" position of FIG. 7, stiffening member 20 can be pivoted relative to first stiffening member 30, as best seen in FIG. 5, in the direction of ARROW "B," to move shield 50 toward the face. However, as best seen in FIGS. 2, 5, 7 and 8, means 60 is provided for limiting the pivoting movement of second stiffening member 30 relative to first stiffening member 20 in the direction of ARROW B (toward the face of wearer 90) so that shield 50 will move no closer to the face of user 90 than is shown in FIGS. 5 and 7, with the head 90 of the wearer shown in phantom. Limiting means 60, as best seen in FIGS. 5, 7 and 8, comprises rectangular void or notch 22 provided in the lower area of end portion 24 of second stiffening member 20 at the crossing of end portion 36 of first stiffening member 30 from a position between band 40 and second stiffening member 20 to a position outside of end portion 24 of second stiffening member 20. Thus notch 22 accepts end portion 36 of first stiffening member 30 to create a "positive" stop. With width "w" of first stiffening member 20 being approximately the same dimension as height "h" of notch 22 (as seen in FIG. 7), stiffening members 20 and 30 will align horizontally as best shown in FIGS. 5 and 8. With this structure, and as best seen in FIGS. 5 and 8, second stiffening member 20 and its attached face shield 50 are prevented or limited from moving in the direction of ARROW "B" past the horizontal or neutral position indicated in FIGS. 5 and 8. This limitation on the movement of face shield 50 caused by the "positive" stopping of means 60 maintains the spacing between stiffening members 20 and 30 (and, therefore, between the face of user 90 and shield 50) as illustrated in FIGS. 2 and 5 and shown as distance "s" in FIGS. 1 and 4 (of course, spacing "s" is not constant, but is greatest at the mid-point of bands 20 and 30 and decreases until the end portions 24 and 36 and 25 and 39 are respectively fastened as described above). This spacing "s" allows ventilation of the face of user 90. As discussed above and best seen in FIGS. 1, 4 and 8, the passing of the end portion 36 of first stiffening member 30 through notch 22 fastens second stiffening member 20 directly to band 40 via fasteners 26 and 32.

As best seen in FIGS. 1, 2, 4 and 5, limiting means 60 need only be provided on one side of face protector 10. On the opposing side, while notch 80 is provided in end portion 25 of second stiffening member 20, stiffening member 20 is fastened at this end portion 25 directly to the end portion 37 of first stiffening member 30 externally thereof with the end portion 37 of first stiffening member 30 being fastened directly to band 40 by means of snap fasteners 28, 29. This notch 80 provides a balance to notch 22 on the opposing side of face protector 10. It has been found through experimentation that a limiting means 60 can be provided on both sides of face protector 10, (and is simply accomplished by moving end portion 37 through notch 80 and fastening end portion 25 to band 40 and then end portion 37 to end portion 25); however, a better balance occurs when limiting means 60 is provided on only one side of face protector 10 and notch 80 is provided on the other side. It has also been found through experimentation that limiting means 60 can be provided on either the left side (as illustrated in the preferred embodiment of FIGS. 1–8) or on the right side (as not illustrated in the drawings) of face protector 10 and the effectiveness is the same.

In an alternate embodiment, best seen in FIGS. 9–16, limiting means 60 is eliminated from the preferred embodiment of FIGS. 1–8 and replaced by notch 160 which is identical to notch 80 of the preferred embodiment and notch 180. Other than this change and the resultant change to the fastening arrangement (eliminating one now extraneous fastener 31 because bands 120 and 130 do not cross at notch 160), the preferred and alternate embodiments are identical. (Numbering in the alternate embodiment in the 100 series corresponds to the same numbering in the preferred embodiment). Turning now to FIGS. 9–16, first stiffening member 130 of face protector 110 can be rotated, in the direction of ARROW "B" through a 180° arc, pivoted about snap fasteners 126, 132 and 128, 129, 134 to the position as best shown in FIGS. 9 and 11. This provides band 140 to be fitted about the head of the user 90, as best seen in FIG. 10. In this arrangement, VELCRO fastening means 142, 144 are provided in the forehead portion of the user and the flexible connecting member 141 is also in the forehead area. This makes for ease of attachment, removal or adjustment by the wearer. In the alternate embodiment of FIGS. 9–16, first stiffening member 130 is pivotally connected to second stiffening member 120 at pivoting fastening members 126, 127, 132 and 128, 129, 134. The first and second stiffening members 120, 130 thus form a second band surrounding or encircling band 140.

As best seen in FIGS. 9, 12, 13 and 15, face shield 150 is connected along its upper portion 152 to second stiffening member 120 by conventional snap or button-type fasteners 146, 148 (similar to that illustrated in the preferred embodiment in FIGS. 1–8, a mid-point snap (not shown) fastener can also be provided between stiffener 120 and face shield 150). In the application of FIGS. 9–16, there is no limiting means (such as means 60 of the preferred embodiment of FIGS. 1–8) for preventing the pivotal movement of second stiffening member 120 (and, therefore, face shield 150) relative to stiffening member 130. The advantage to this alternate embodiment is that face protector 10 can be more easily applied, removed or adjusted by the wearer since fastener means 142, 144 are at the user's forehead.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A face protector for shielding the face of the wearer while permitting observation and pivoting of the shield toward and away from the face comprising:
   (a) an elongated flexible band sized and adapted to be fitted about the head;
   (b) a first elongated flexible stiffening member attached therealong to a corresponding confronting portion of said band;
   (c) a second elongated stiffening member having a length greater than said first stiffening member and pivotally attached to said first stiffening member at corresponding end portions of said stiffening members, whereby said stiffening members are spaced apart when said band is fitted about said head as aforestated;
   (d) a transparent face shield connected along the top portion thereof to said second stiffening member, whereby pivotal movement of said second stiffening member relative to said first member permits movement of said shield toward and away from the face; and,
   (e) means for limiting the pivoting movement of said second stiffening member relative to said first stiffening member and said shield toward the face comprising:
      i. a void provided in at least one end portion of said second stiffening member; and,
      ii. means for fastening said one end portion of said second stiffening member between the corresponding end portion of said first stiffening member and said band.

2. The face protector of claim 1, wherein said band is made of absorbent padding.

3. The face protector of claim 1, wherein said band includes fastening means for maintaining said band about the head of the wearer.

4. The face protector of claim 1, wherein said face shield is adapted in size and shape to fit over at least the eyes of the wearer.

5. The face protector of claim 1, wherein said face shield is of a plastic material coated with an anti-fogging agent to prevent the wearer's breath from fogging the shield when said face protector is worn.

6. The face protector of claim 1, wherein said face shield is of a plastic material coated with an anti-glare agent to prevent glare from impeding the wearer's vision when the face protector is worn.

7. A face protector for shielding the face of the wearer while permitting observation and pivoting of the shield toward and away from the face comprising:
   (a) an elongated flexible band sized and adapted to be fitted about the head;

(b) a first elongated flexible stiffening member attached therealong to a corresponding confronting exterior portion of said band;

(c) a second elongated stiffening member having a length greater than said first stiffening member and pivotally attached exteriorly of and to said first stiffening member at corresponding end portions of said stiffening members, whereby said stiffening members are spaced apart when said band is fitted about said head as aforestated;

(d) a transparent face shield connected along the top portion thereof to the exterior surface of said second stiffening member, whereby pivotal movement of said second stiffening member relative to said first member permits movement of said shield toward and away from the face; and, (e) means for limiting the pivoting movement of said second stiffening member relative to said first stiffening member and said shield toward the face comprising:

i. a void provided in at least one end portion of said second stiffening member; and, ii. means for the fastening said one end portion of said second stiffening member between the corresponding end portion of said first stiffening member and said band, whereby said void accepts said corresponding end portion of said first stiffening member.

8. The face protector of claim 7, wherein said band is made of absorbent padding.

9. The face protector of claim 7, wherein said band includes fastening means for maintaining said band about the head of the wearer.

10. The face protector of claim 7, wherein said face shield is adapted in size and shape to fit over at least the eyes of the wearer.

11. The face protector of claim 7, wherein said face shield is of a plastic material coated with an anti-fogging agent to prevent the wearer's breath from fogging the shield when said face protector is worn.

12. The face protector of claim 7, wherein said face shield is of a plastic material coated with an anti-glare agent to prevent glare from impeding the wearer's vision when the face protector is worn.

13. The face protector of claims 7, wherein said void provided in said one end portion of said second stiffening member has a vertical dimension substantially equal to the vertical dimension of said first stiffening member.

14. A face protector for shielding the face of the wearer while permitting observation and pivoting of the shield toward and away from the face comprising:

(a) an elongated generally rectangular flexible band adapted to be fitted about the head;

(b) a first elongated generally rectangular flexible stiffening member having a length less than said band and attached therealong to a corresponding confronting exterior portion of said band;

(c) a second elongated generally rectangular stiffening member having a length greater than said first stiffening member and pivotally attached exteriorly of and to said first stiffening member at corresponding end portions of said stiffening members, whereby said stiffening members are spaced apart when said band is fitted about said head as aforestated;

(d) a transparent face shield connected along the top portion thereof to the exterior surface of said second stiffening member, whereby pivotal movement of said second stiffening member relative to said first member permits movement of said shield toward and away from the face; and, (e) means for limiting the pivoting movement of said second stiffening member relative to said first stiffening member and said shield toward the face comprising:

i. a void provided in at least one end portion of said second stiffening member, said void having a vertical dimension substantially equal to the vertical dimension of said first stiffening member, and, ii. means for fastening said one end portion of said second stiffening member between the corresponding end portion of said first stiffening member and said band, whereby said void accepts said corresponding end portion of said first stiffening member.

15. The face protector of claim 14, wherein said hand is made of absorbent padding.

16. The face protector of claim 14 wherein said first and second stiffening members are made of plastic.

17. The face protector of claim 14, wherein said band includes fastening means for maintaining said hand about the head of the wearer.

18. The face protector of claim 14, wherein said face shield is adapted in size and shape to fit over at least the eyes of the wearer.

19. The face protector of claim 14, wherein said face shield is of a plastic material coated with anti-fogging and anti-glare agents to prevent the wearer's breath from fogging the shield and to prevent glare from impeding the wearer's vision when the face protector is worn.

* * * * *